United States Patent [19]

Eggensperger et al.

[11] Patent Number: 5,670,160

[45] Date of Patent: Sep. 23, 1997

[54] PRESERVATIVES AND THEIR USE

[75] Inventors: Heinz Eggensperger, Hamburg; Karl-Heinz Diehl, Norderstedt; Peter Oltmanns, Hamburg, all of Germany

[73] Assignee: Schülke & Mayr GmbH, Hamburg, Germany

[21] Appl. No.: 649,254

[22] Filed: Jan. 30, 1996

Related U.S. Application Data

[63] Continuation of Ser. No. 115,298, Sep. 1, 1993, abandoned, which is a continuation-in-part of Ser. No. 741,008, Aug. 6, 1991, abandoned.

[30] Foreign Application Priority Data

Aug. 24, 1990 [DE] Germany ............... 40 26 756.3

[51] Int. Cl.$^6$ ............... A01N 25/00; A01N 25/02
[52] U.S. Cl. ............... 424/405; 252/380; 424/76.8
[58] Field of Search ............... 424/405, 76.8; 422/28; 252/380, 106

[56] References Cited

U.S. PATENT DOCUMENTS

| | | | |
|---|---|---|---|
| 4,767,788 | 8/1988 | Diana | 514/574 |
| 4,836,986 | 6/1989 | Ogunbiyi et al. | 422/28 |
| 4,851,433 | 7/1989 | Kraus | 514/648 |
| 4,900,721 | 2/1990 | Bansemir et al. | 514/25 |
| 4,942,041 | 7/1990 | Guhl et la. | 424/613 |
| 5,015,471 | 5/1991 | Birtwistle et al. | 424/70 |
| 5,049,587 | 9/1991 | Okamoto et al. | 514/653 |
| 5,063,044 | 11/1991 | Kohl et al. | 424/70 |
| 5,124,392 | 6/1992 | Robertson et al. | 424/427 |
| 5,137,728 | 8/1992 | Bawa | 424/427 |
| 5,153,179 | 10/1992 | Eibl | 514/34 |

FOREIGN PATENT DOCUMENTS 57-9717  1/1982  Japan .

OTHER PUBLICATIONS

Merck Index, 10th Ed., (1983) Windholtz et al. Editors, pp. 413 and 1046.

Primary Examiner—Melvyn I. Marquis
Assistant Examiner—Robert H. Harrison
Attorney, Agent, or Firm—Fish & Richardson P.C.

[57] ABSTRACT

A preservative, for compositions having an aqueous phase, comprising a) 5 to 60% by weight of an organic acid selected from the group consisting of benzoic acid, 4-hydroxybenzoic acid, salicylic acid, formic acid, acetic acid, propionic acid, sorbic acid, undecylenic acid and dehydracetic acid or their mixtures including their sodium, potassium, calcium, magnesium, ammonium and ethanolamine salts b) 10 to 95% by weight of alcohols of the general formulae I, II or III

I)

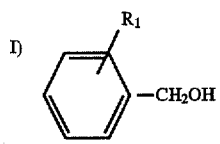

II)

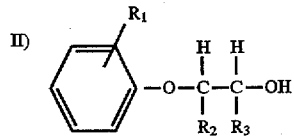

III)

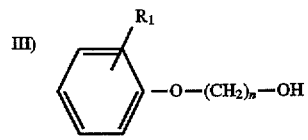

in which $R_1$ denotes hydrogen, an n-alkyl, iso-alkyl or alkoxy radical having 1 to 3 C atoms, and $R_2$ and $R_3$ denote hydrogen or a $CH_3$— or $C_2H_5$— radical and n has the value of 3 or 4, and c) 0.1 to 20% by weight of one or more poly(hexamethylenebiguanide) salts of the general formula

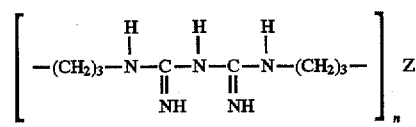

in which Z represents hydrochloride, acetate, lactate, benzoate, propionate, 4-hydroxybenzoate, sorbate or salicylate; and n has the value of 4 to 6, in combination in a customary carrier or solvent.

8 Claims, No Drawings

PRESERVATIVES AND THEIR USE

This application is a continuation of application Ser. No. 08/115,298 filed on Sep. 1, 1993, which was a continuation-in-part of application Ser. No. 07/741,008 filed on Aug. 6, 1991, both now abandoned.

FIELD OF THE INVENTION

The invention relates to a preservative for products with an aqueous phase.

BACKGROUND OF THE INVENTION

The use of formaldehyde and formaldehyde-deposit substances and other preservatives such as isothiazolinones is not desirable because of their poor environmental compatibility and because they are toxic to humans. Furthermore, there are mentioned in K. H. Wallhäusser "Praxis der Sterilisation, Desinfektion and Konservierung" [Sterilization, Disinfection and Preservation in Practice], 4th Ed. (1988) and in H. P. Fiedler "Lexikon der Hilfsstoffe fur Pharmazie, Kosmetik und angrenzende Gebiete" [Encyclopedia of the Auxiliaries for Pharmacy, Cosmetics and Related Fields], 3rd Ed. (1989) a large number of individual preservatives such as, organic acids, phenyl compounds or guanidines and a large number of other compounds. It would be advantageous to formulate from these individual preservatives, highly specific synergistic preservative combinations.

It was the object of the invention to propose a novel preservative on the basis of a synergistically acting three-component or multi-component system for products or systems with an aqueous phase, which shows a broad antimicrobial spectrum of action even when used at low concentrations.

SUMMARY OF THE INVENTION

This objective is achieved with the present invention which provides a three-component system comprising a preservative, for compositions having an aqueous phase, comprising a) 5 to 60% by weight of an organic acid selected from the group consisting of benzoic acid, 4-hydroxybenzoic acid, salicylic acid, formic acid, acetic acid, propionic acid, sorbic acid, undecylenic acid and dehydroacetic acid or their mixtures including their sodium, potassium, calcium, magnesium, ammonium and ethanolamine salts b) 10 to 95% by weight of alcohols of the general formula I, II or III

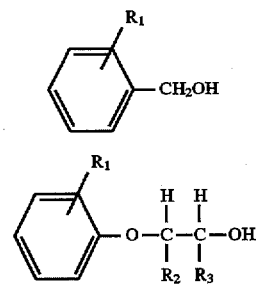

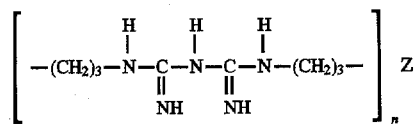

in which $R_1$ denotes hydrogen, an n-alkyl, iso-alkyl or alkoxy radical having 1 to 3 C atoms, and $R_2$ and $R_3$ denote hydrogen or a $CH_3$— or $C_2H_5$— radical and n has the value of 3 or 4, and c) 0.1 to 20% by weight of one or more poly (hexamethylenebiguanide) salts of the general formula

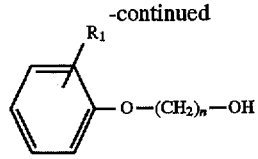

in which Z represents hydrochloride, acetate, lactate, benzoate, propionate, 4-hydroxybenzoate, sorbate or salicylate; and n has the value of 4 to 6, in combination in a customary carrier or solvent.

In principle, this preservative according to the patent contains, as the synergistic active substances, a mixture of at least a) one organic acid, b) one monophenyl glycol ether and c) one guanidine derivative.

This invention provides preservatives having synergistic activity on shampoos, creams, lotions, i.e. for cosmetic products for rinse-off and leave-on application, and for products in the field of the detergents and cleaners, such as washing-up products and fabric conditioners, and formulations for topical administration from the pharmaceutical sector.

DETAILS OF THE INVENTION

This synergistic combination shows a surprisingly high effectiveness, in particular taking into account that the organic acids which are listed in Appendix 6 of the European Cosmetics Regulations, such as sorbic acid or salicylic acid, are effective mainly against yeasts and molds in comparatively high concentrations in undissociated form only, and their activity against bacteria is only low. In addition, neither monophenyl glycol ethers such as phenoxyethanol or phenoxypropanol nor other alcohols such as benzyl alcohol, when used on their own, show a sufficient antimicrobial activity in an acceptable range of concentrations.

In consequence, it is surprising that a concentration of an organic acid with a monophenyl glycol ether or benzyl alcohol and with polyhexamethylenebiguanide has an excellent preserving action for products or systems with an aqueous phase.

What is particularly surprising is the property of the three-component preservative according to the invention that, its combination with complexants or alkyl glycol ethers results in a further synergistic enhanced action. A further surprising property of the preservative which, according to the invention, consists of three classes of active substances, is the fact that, in combination with other preservatives which are known per se, such as chloroallyladamantane, p-hydroxybenzoic ester, 1,2-dibromo-2,4-dicyanobutane, 2-bromo-2-nitropropane-1,3-diol, 5-bromo-5-nitro-1,3-dioxane and formaldehyde-deposit substances, a further synergistic enhanced activity can be achieved. As component a), organic acids are used which correspond to the general formula RCOOH, it being possible for R to have the following meaning:

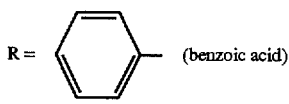 (benzoic acid)

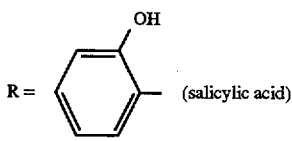 (salicylic acid)

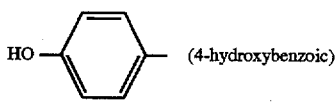 (4-hydroxybenzoic)

R = H (formic acid)
R = $CH_3$— (acetic acid)
R = $CH_3$—$CH_2$— (propionic acid)
R = $CH_3$—CH=CH—CH=CH— (sorbic acid)
5r = $CH_2$=CH—$(CH_2)_8$— (unndecylenic acid)
and/or dehydroacetic acid

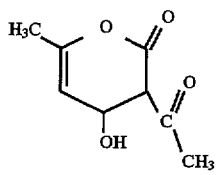

and their sodium, potassium, calcium, magnesium, ammonium or ethanolamine salts.

This component a) is employed in amounts of 5 to 60% by weight, namely preferably in amounts of 10 to 30% by weight. The particularly preferred representative of these acids is benzoic acid. The amounts given here and in what follows in each case relate to the actual active substances of the synergistic preservative mixture.

As component b), there are employed 10 to 95 and preferably 40 to 80% by weight of one or more alcohols of the following general formula I to III:

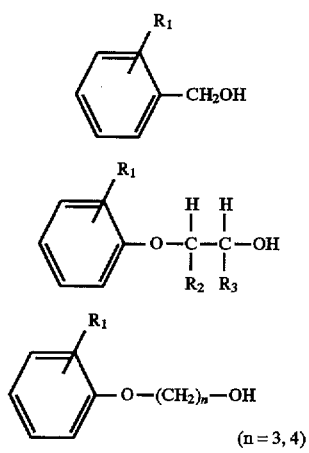

in which $R_1$ is an H atom, n-alkyl or iso-alkyl or alkoxy with 1 to 3 C atoms, and $R_2$ and $R_3$ are an H atom or a $CH_3$— or $C_2H_5$— group and n has the value of 3 or 4.

These alcohols are preferably employed in amounts of 40 to 80% by weight, the alcohols of the general formula I and II being preferred.

As component c), there are employed polyhexamethylenebiguanide salts of the general formula

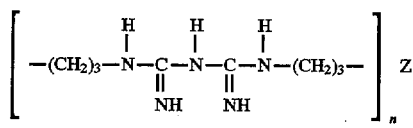

in which Z represents hydrochloride, acetate, lactate, benzoate, propionate, 4-hydroxybenzoate, sorbate or salicylate; and n has the value of 4 to 6, in combination in a customary carrier or solvent.

The preferred salts are the hydrochloride, lactate and benzoate.

In a particularly preferred embodiment of the preservative according to the invention which consists of the three above-mentioned synergistically acting components a), b) and c), there is added, as a further synergistically active component d), a substituted glycol ether in an amount of 0.1 to 20 and preferably in an amount of 0.5 to 10% by weight, the glycerol ether having the following general formula with the substituents listed:

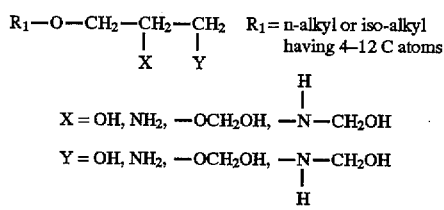

In a further, likewise preferred embodiment of the invention, the preservative consisting of components a), b) and c) and, if desired, d), can also contain, as a further component e), an alkyl ether of the following general formula in an amount of 0.1 to 20 and preferably 0.5 to 10% by weight.

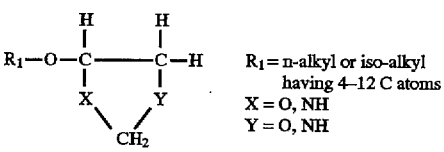

Finally, the synergistically acting preservative which consists of the three components a), b) and c), if desired together with the further components d) and/or e), can also contain complexants such as ethylenediaminetetraacetic acid (EDTA) and its salts, or nitrilotriacetic acid (NTA), aminoglycine derivatives, serinediacetic acid or isoserinediacetic acid.

The synergistic enhanced effect is also when the preservative contains further biocides such as chloroallyladamantane, p-hydroxybenzoic ester, 1,2-dibromo -2,4-dicyanobutane, 2-bromo-2-nitropropane-1,3-diol, 5-bromo-5-nitro-1,3-dioxane and also imidazolidinurea and/or hydantoin derivatives, namely preferably in an amount of from 1 to 20% by weight.

The preservatives as claimed in the patent can be added to the products to be preserved such as cosmetic and pharmaceutical products or products with a cleaning action, in the form of their individual components, as a mixture or as a concentrate in a solvent, the concentration, based on the product to be preserved, being in a range of 0.01 to 2% by weight, preferably 0.1 to 0.3%, in each case based on the active substances.

The preparations according to the invention can be obtained with ease by combining the individual components.

However, it may be advantageous to replace one part of the alcohol components by a further solvent, for example for increasing stability to low temperatures on storage or on transport. Suitable solvents beside water are glycols such as propylene glycol, dipropylene glycol, triethylene glycol or glycol ethers such as butyl diglycol.

EXAMPLE

The synergistic enhancement of activity of the preparations according to the invention is demonstrated by the results from a preservative stress test using two different water-containing systems. The test procedure described below in greater detail was made difficult inasmuch as the PseudoNonas microorganisms mentioned, which are a problem in practice, are species which were adapted to both substrates (*Ps. cepacia, Ps. putida, Ps. stutzeri*).

The test described below is carried out to determine the preserving action of chemical preservatives in water-containing products or systems, the principle of the method described reflecting the effectiveness of chemical preservatives as regards their preservation of containers of water-containing products/systems under the conditions of the user's practice. For this purpose, various tests are set up in which the preservatives to be examined are added at different concentrations to the unpreserved samples. A consistent microbial stress is effected by periodically inoculating the test batches. In parallel with the inoculation, samples of the individual batches just before inoculation are plated. The assessment is carried out by means of the microbial growth of the samples plated. The longer the period before the first occurrence of microbial growth, the more effective the preservative.

To carry out these tests, 25 g samples of the product to be tested were weighed into screw-topped jars. The preservatives to be tested are added at their use concentrations, in each case to separate batches. An unpreserved product sample is used in each case as a growth control. Two days after the preservatives were added, the samples are infected with 0.1 ml of inoculation solution. The titer of this inoculation solution should be between 108 and 10' microorganisms/mi. The following microorganisms are test organisms for the preservation stress test:

Bacteria:
  *Escherichia coli*
  *Staphylococcus aureus*
  *Pseudomonas aeruginosa*
  Pseudomonas species which cause problems in practice
Yeasts:
  *Candida albicans*
Molds: *Aspergillus niger*

The test batches are subsequently inoculated once per week and plated onto agar plates once per week, the first plating being carried out just before reinoculation. The microbial growth of the plated samples is assessed after a three-day incubation time at 25° C. To be on the safe side, negative plated samples are observed for a further three days and reassessed. The preserving action of the individual product concentrations is assessed by a semiquantitative method on the basis of the growth of the individual plated samples, using a key from − via + to +++. The results of the preservation is determinedly massive, i.e. +++ microbial growth which has been determined several times. The test is carried out for a maximum of ten weeks.

When the results are assessed, this is done on the basis that a preservative is to be assessed as good when it lasts under the above-described laboratory conditions over a period of six weeks without the batches being contaminated, i.e. when no microbial growth can be detected after the sixth inoculation.

To demonstrate the surprising enhancement of action of the preparations according to the invention, the test was extended to ten weeks, i.e. ten inoculation cycles.

The water-containing products used for the determination of the antimicrobial activity are the formulations, which are described below of a shampoo (A) and a day cream (oil-in-water) (B), of the following composition:

|  | Concentration [% w/w] |
|---|---|
| A. Shampoo |  |
| Alkyl ether sulfate + nonionic emulsifier | 15.30 |
| Fatty acid/polypeptide condensate | 18.80 |
| Lauric acid monoglyceride | 1.00 |
| Perfume | 0.30 |
| Sodium chloride | 1.60 |
| Water | to 100.00 |
| Preservative | 10.00 |
| B. Day cream |  |
| Polyoxyethylene fatty acid ester | 6.00 |
| Cetyl alcohol | 1.00 |
| Stearic acid | 5.00 |
| Paraffin oil | 4.00 |
| Octyldodecanol | 3.00 |
| Glycerol | 3.80 |
| Water | to 100.00 |
| Perfume | 0.30 |
| Preservative |  |

Table I below indicates the effectiveness of the individual components with regard to their concentration in ppm, expressed by the inoculation cycles without growth achieved in the microorganism stress test, to be more precise for two typical representatives of component a), namely benzoic acid and dehydroacetic acid, and furthermore for one typical representative of the alcohols, namely for 2-phenoxyethanol and furthermore for one typical representative of component c), namely for a polyhexamethylenebiguanide hydrochloride and, finally, also for the further component d), namely the substituted glycerol ether.

A comparison of the values of Table I below with those of Table II shows that the activity of the individual components at the same application concentration is surpassed by each of the combinations given of the three-component system as claimed in the patent, consisting of acid, alcohol and guanidine derivative, which confirms a synergistic effect which is actually present.

A comparative study of the results from Table II with those of Table III illustrates the enhanced effectiveness of the transition to the four-component system of Table III, where the glycerol ether is additionally present. As again shown by a comparison with Table I, the fact that the activity of the combinations is greater in each individual case than that of the individual active substances at the same concentration, is also true for the four-component system.

Corresponding information can be seen in Tables IV–IX, which represent the results which were determined when other examples of in each case the three-component and the corresponding four-component system in the shampoo (Table pairs IV/V and VIII/IX) and in the day cream (Table pair VI/VII) are subjected to the microorganism stress test.

TABLE I

| Concentration [ppm] | Benzoic Acid DC | Benzoic Acid SH | Dehydro-acetic Acid DC | Dehydro-acetic Acid SH | 2-Phenoxy-ethanol DC | 2-Phenoxy-ethanol SH | PHMBG DC | PHMBG SH | $C_7$-GE DC | $C_7$-GE SH |
|---|---|---|---|---|---|---|---|---|---|---|
| 10,000 | 9 | 10 | 5 | 7 | 6 | 5 | 10 | 0 | 6 | 4 |
| 8,000 | 8 | 9 | 4 | 5 | 5 | 5 | 10 |   | 5 | 3 |
| 6,000 | 6 | 8 | 3 | 4 | 4 | 3 | 10 |   | 3 | 2 |
| 5,000 | 5 | 7 | 1 | 2 | 2 | 2 | 10 |   | 3 | 1 |
| 4,000 | 4 | 5 | 0 | 1 | 1 | 0 | 8 |   | 1 | 0 |
| 3,000 | 2 | 4 |   | 0 | 0 |   | 7 |   | 0 |   |
| 2,500 | 1 | 2 |   |   |   |   | 6 |   |   |   |
| 2,000 | 0 | 1 |   |   |   |   | 5 |   |   |   |
| 1,500 |   | 0 |   |   |   |   | 3 |   |   |   |
| 1,000 |   |   |   |   |   |   | 2 |   |   |   |
| 750 |   |   |   |   |   |   | 1 |   |   |   |
| 500 |   |   |   |   |   |   | 0 |   |   |   |

PHMBG = polyhexamethylenobiguanide hydrochloride
$C_7$-GE = 3-heptyloxypropane-1,2-diol ($C_7$-glycol ether)
DC = day cream
SH = shampoo

TABLE II

Day Cream

Concentration [ppm]

| | | | | | | | | | | | | |
|---|---|---|---|---|---|---|---|---|---|---|---|---|
| Benzoic acid | 100 | 200 | 300 | 400 | 500 | 600 | 200 | 200 | 200 | 200 | 200 | 200 |
| 2-Phenoxyethanol | 350 | 700 | 1,050 | 1,400 | 1,750 | 2,100 | 700 | 700 | 700 | 700 | 700 | 700 |
| PHMBG | 5 | 10 | 15 | 20 | 25 | 30 | 100 | 200 | 400 | 800 | 1,600 | 3,200 |
| Inoculation cycles | 2 | 4 | 5 | 7 | 9 | 10 | 4 | 5 | 6 | 8 | 9 | 10 |
| Benzoic acid | 200 | 400 | 800 | 1,600 | 3,200 | | 800 | 800 | 800 | 800 | 800 | |
| 2-Phenoxyethanol | 600 | 600 | 600 | 600 | 600 | | 800 | 800 | 800 | 800 | 800 | |
| PHMBG | 500 | 400 | 300 | 200 | 100 | | 20 | 40 | 80 | 160 | 320 | |
| Inoculation cycles | 7 | 7 | 7 | 9 | 10 | | 4 | 5 | 6 | 6 | 8 | |

PHMBG = polyhexamethylenebiguanide hydrochloride

TABLE III

Day Cream

Concentration [ppm]

| | | | | | | | | | | | | |
|---|---|---|---|---|---|---|---|---|---|---|---|---|
| Benzoic acid | 100 | 200 | 300 | 400 | 500 | 600 | 200 | 200 | 200 | 200 | 200 | 200 |
| 2-Phenoxyethanol | 350 | 700 | 1,050 | 1,400 | 1,750 | 2,100 | 700 | 700 | 700 | 700 | 700 | 700 |
| PHMBG | 5 | 10 | 15 | 20 | 25 | 30 | 100 | 200 | 400 | 800 | 1,600 | 3,200 |
| $C_7$-glycol ether | 200 | 200 | 200 | 200 | 200 | 200 | 300 | 300 | 300 | 300 | 200 | 200 |
| Inoculation cycles | 3 | 5 | 7 | 8 | 10 | 10 | 7 | 8 | 9 | 10 | 10 | 10 |
| Benzoic acid | 200 | 400 | 800 | 1,600 | 3,200 | | 800 | 800 | 800 | 800 | 800 | |
| 2-Phenoxyethanol | 600 | 600 | 600 | 600 | 600 | | 800 | 800 | 800 | 800 | 800 | |
| PHMBG | 500 | 400 | 300 | 200 | 100 | | 20 | 40 | 80 | 160 | 320 | |
| $C_7$-glycol ether | 300 | 300 | 200 | 100 | 100 | | 200 | 200 | 200 | 200 | 200 | |
| Inoculation cycles | 9 | 9 | 9 | 10 | 10 | | 5 | 6 | 8 | 9 | 10 | |

PHMBG = polyhexamethylenebiguanide hydrochloride
$C_7$-glycol ether = 3-heptyloxy-propane-1,2-diol

TABLE IV

Shampoo

| | Concentration [ppm] | | | | | | | | | | | | |
|---|---|---|---|---|---|---|---|---|---|---|---|---|---|
| Benzoic acid | 500 | 1,000 | 1,500 | 2,000 | 2,500 | 600 | 600 | 600 | 600 | 1,200 | 1,200 | 1,200 | 1,200 |
| 2-Phenyloxyethanol | 1,000 | 1,000 | 1,500 | 1,500 | 1,500 | 2,000 | 2,000 | 2,000 | 2,000 | 2,000 | 2,000 | 2,000 | 2,000 |
| PHMBG | 100 | 100 | 100 | 100 | 100 | 100 | 200 | 300 | 400 | 100 | 200 | 300 | 400 |
| Inoculation cycles | 2 | 3 | 5 | 7 | 9 | 4 | 5 | 6 | 7 | 6 | 6 | 8 | 8 |

PHMBG = polyhexamethylenebiguanide hydrochloride

TABLE V

Shampoo

| | Concentration [ppm] | | | | | | | | | | | | |
|---|---|---|---|---|---|---|---|---|---|---|---|---|---|
| Benzoic acid | 500 | 1,000 | 1,500 | 2,000 | 2,500 | 600 | 600 | 600 | 600 | 1,200 | 1,200 | 1,200 | 1,200 |
| 2-Phenoxyethanol | 1,000 | 1,000 | 1,500 | 1,500 | 1,500 | 2,000 | 2,000 | 2,000 | 2,000 | 2,000 | 2,000 | 2,000 | 2,000 |
| PHMBG | 100 | 100 | 100 | 100 | 100 | 100 | 100 | 300 | 400 | 100 | 200 | 300 | 400 |
| $C_7$-glycol ether | 300 | 300 | 300 | 300 | 300 | 400 | 400 | 400 | 400 | 500 | 400 | 300 | 200 |
| Inoculation cycles | 3 | 5 | 7 | 8 | 10 | 5 | 6 | 8 | 9 | 8 | 8 | 10 | 10 |

PHMBG = polyhexamethylenebiguanide hydrochloride
$C_7$-glycol ether = 3-(heptyloxy)-Propane-1,2-diol

TABLE VI

Day Cream

| | Concentration [ppm] | | | | | | | | |
|---|---|---|---|---|---|---|---|---|---|
| Dehydroacetic acid | 200 | 300 | 400 | 500 | | 300 | 300 | 300 | 300 |
| 2-Phenoxyethanol | 700 | 1,500 | 1,400 | 1,750 | | 600 | 600 | 600 | 600 |
| PHMBG | 10 | 15 | 20 | 25 | | 100 | 200 | 400 | 800 |
| Inoculation cycles | 3 | 4 | 5 | 7 | | 4 | 5 | 6 | 7 |
| Dehydroacetic acid | 100 | 200 | 400 | 800 | 1,600 | 200 | 400 | 600 | 800 |
| Benzoic acid | 100 | 200 | 400 | 800 | 1,600 | 800 | 600 | 400 | 200 |
| 2-Phenoxyethanol | 600 | 600 | 600 | 600 | 600 | 800 | 800 | 800 | 800 |
| PHMBG | 500 | 400 | 300 | 200 | 100 | 100 | 100 | 100 | 100 |
| Inoculation cycle | 6 | 6 | 5 | 7 | 9 | 7 | 7 | 6 | 5 |

PHMBG = polyhexamethylenebiguanide hydrochloride

TABLE VII

Day Cream

| | Concentration [ppm] | | | | | | | | |
|---|---|---|---|---|---|---|---|---|---|
| Dehydroacetic acid | 200 | 300 | 400 | 500 | | 300 | 300 | 300 | 300 |
| 2-Phenoxyethanol | 700 | 1,500 | 1,400 | 1,750 | | 600 | 600 | 600 | 600 |
| PHMBG | 10 | 15 | 20 | 25 | | 100 | 200 | 400 | 800 |
| $C_7$-glycol ether | 200 | 200 | 200 | 200 | | 300 | 300 | 300 | 300 |
| Inoculation cycles | 4 | 6 | 7 | 9 | | 6 | 7 | 9 | 9 |
| Dehydroacetic acid | 100 | 200 | 400 | 800 | 1,600 | 200 | 400 | 600 | 800 |
| Benzoic acid | 100 | 200 | 400 | 800 | 1,600 | 800 | 600 | 400 | 200 |
| 2-Phenoxyethanol | 600 | 600 | 600 | 600 | 600 | 800 | 800 | 800 | 800 |
| PHMBG | 500 | 400 | 300 | 200 | 100 | 100 | 100 | 100 | 100 |
| $C_7$-glycol ether | 300 | 300 | 200 | 100 | 100 | 200 | 200 | 200 | 200 |
| Inoculation cycles | 8 | 8 | 7 | 9 | 10 | 10 | 9 | 8 | 8 |

PHMBG = polyhexamethylenebiguanide hydrochloride
$C_7$-glycol ether = 3-(heptyloxy)propane-1,2-diol

TABLE VIII

Shampoo

Concentration [ppm]

| Dehydroacetic acid | 1,000 | 1,500 | 2,000 | 2,500 | 3,000 | 2,000 | 2,000 | 2,000 | 2,000 | 2,000 |
|---|---|---|---|---|---|---|---|---|---|---|
| 2-Phenoxyethanol | 1,000 | 1,000 | 1,000 | 1,000 | 1,000 | 2,000 | 2,000 | 2,000 | 2,000 | 2,000 |
| PHMBG | 100 | 100 | 100 | 100 | 100 | 200 | 400 | 600 | 800 | 1,000 |
| Inoculation cycles | 0 | 1 | 2 | 2 | 3 | 3 | 4 | 4 | 5 | 6 |

| Dehydroacetic acid | 2,000 | 1,500 | 1,000 | 500 | | 1,000 | 1,000 | 1,000 | 1,000 |
|---|---|---|---|---|---|---|---|---|---|
| Benzoic acid | 500 | 1,000 | 1,500 | 2,000 | | 1,000 | 1,000 | 1,000 | 1,000 |
| 2-Phenoxyethanol | 1,500 | 1,500 | 1,500 | 1,500 | | 900 | 700 | 500 | 300 |
| PHMBG | 100 | 100 | 100 | 100 | | 100 | 300 | 500 | 700 |
| Inoculation cycles | 6 | 7 | 8 | 10 | | 6 | 8 | 9 | 10 |

PHMBG = polyhexamethylenebiguanide hydrochloride

TABLE IX

Shampoo

Concentration [ppm]

| Dehydroacetic acid | 1,000 | 1,500 | 2,000 | 2,500 | 3,000 | 2,000 | 2,000 | 2,000 | 2,000 | 2,000 |
|---|---|---|---|---|---|---|---|---|---|---|
| 2-Phenoxyethanol | 1,000 | 1.000 | 1,000 | 1,000 | 1,000 | 2,000 | 2,000 | 2,000 | 2,000 | 2,000 |
| PHMBG | 100 | 100 | 100 | 100 | 100 | 200 | 400 | 600 | 800 | 1,000 |
| $C_7$-glycol ether | 400 | 400 | 400 | 400 | 400 | 300 | 300 | 300 | 300 | 300 |
| Inoculation cycles | 2 | 2 | 3 | 4 | 5 | 4 | 6 | 7 | 7 | 9 |

| Dehydroacetic acid | 2,000 | 1,500 | 1,000 | 500 | | 1,000 | 1,000 | 1,000 | 1,000 |
|---|---|---|---|---|---|---|---|---|---|
| Benzoic acid | 500 | 1,000 | 1,500 | 2,000 | | 1,000 | 1,000 | 1,000 | 1,000 |
| 2-Phenoxyethanol | 1,500 | 1,500 | 1,500 | 1,500 | | 900 | 700 | 500 | 300 |
| PHMBG | 100 | 100 | 100 | 100 | | 100 | 300 | 500 | 700 |
| $C_7$-glycol ether | 300 | 300 | 300 | 300 | | | | | |
| Inoculation cycles | 8 | 8 | 10 | 10 | | 8 | 10 | 10 | 10 |

PHMBG = polyhexamethylenebiguanide hydrochloride
$C_7$-glycol ether = 3-(heptyloxy)propane-1,2-diol Starting from the above recognition of the synergistic action of components a), b) and c) and the further enhancement of action by components d) and e), the following preparations were prepared.

Example 1

A preservative with the following components was prepared:

| | [% by weight] |
|---|---|
| Dehydroacetic acid | 10 |
| Benzoic acid | 10 |
| PHMBG | 1 |
| Water | 4 |
| Benzyl alcohol | 36 |
| 2-Phenoxyethanol | 21 |
| Dipropylene glycol | 18 |

This example represents the three-component system according to the invention which has a synergistic action, and which consists of acids, alcohols and the guanidine derivative.

The preservatives of Examples 2 and 3 additionally contain, as further active substances, p-hydroxybenzoic esters, while having a reduced acid content in comparison with Example 1.

Example 2

| | [% by weight] |
|---|---|
| Dehydroacetic acid | 3 |
| Undecylenic acid | 4 |
| Ethyl p-hydroxybenzoate | 8 |
| Propyl p-hydroxybenzoate | 4 |
| Butyl p-hydroxybenzoate | 2 |
| PHMBG | 1 |
| Triethylene glycol | 59 |
| Water | 4 |
| Benzyl alcohol | 15 |

Example 3

| | [% by weight] |
|---|---|
| Dehydroacetic acid | 3 |
| Benzoic acid | 4 |
| Ethyl p-hydroxybenzoate | 8 |
| Propyl p-hydroxybenzoate | 4 |
| Butyl p-hydroxybenzoate | 2 |
| PHMBG | 1 |
| Triethylene glycol | 59 |
| Water | 4 |
| Benzyl alcohol | 15 |

In general, 0.2–0.3% of these preparations, based on the product to be preserved, is adequate for sufficiently protecting for example cosmetic products against microbial degradation.

In the preparations of Examples 4–9, an additional solvent was largely dispensed with. The higher content of the alcohol components was noticeable by an enhanced action in comparison with the preservative of Example 1.

Example 4

|  | [% by weight] |
| --- | --- |
| Dehydroacetic acid | 10 |
| Benzoic acid | 10 |
| PHMBG | 1 |
| Water | 4 |
| 2-Phenoxyethanol | 75 |

Example 5

|  | [% by weight] |
| --- | --- |
| Dehydroacetic acid | 10 |
| Benzoic acid | 10 |
| Butyl p-hydroxybenzoate | 2 |
| PHMBG | 1 |
| Water | 4 |
| 2-Phenoxyethanol | 73 |

Example 6

|  | [% by weight] |
| --- | --- |
| Dehydroacetic acid | 10 |
| Benzoic acid | 10 |
| PHMBG | 1 |
| Benzyl alcohol | 79 |

Example 7

|  | [% by weight] |
| --- | --- |
| Dehydroacetic acid | 10 |
| Benzoic acid | 10 |
| PHMBG | 1 |
| Water | 4 |
| Benzyl alcohol | 37.5 |
| Phenoxypropanol | 37.5 |

Example 8

|  | [% by weight] |
| --- | --- |
| Dehydroacetic acid | 10 |
| Benzoic acid | 10 |
| PHMBG | 2 |
| Water | 6 |
| Benzyl alcohol | 25 |
| 2-Phenoxyethanol | 47 |

EXAMPLE 9

|  | [% by weight] |
| --- | --- |
| Dehydroacetic acid | 10 |
| Benzoic acid | 10 |
| PHMBG | 3 |
| Water | 8 |
| Benzyl alcohol | 44 |
| 2-Phenoxyethanol | 25 |

In this series, Example 9 is particularly suitable as a high-performance preparation for the preservation of those o/w or w/o emulsions which make particular demands on the preservative because of their structure and/or their ingredients.

Examples 10–14 additionally contain in each case one representative from the series of the glycerol ethers as the fourth component. In general, a sufficiently high preservation is achieved with these preparations even when application concentrations of 0.1–0.2%, relative to the product to be preserved, are used because of the further enhancement of action achieved by this fourth component.

Example 10

|  | [% by weight] |
| --- | --- |
| Dehydroacetic acid | 10 |
| Benzoic acid | 10 |
| PHMBG | 1 |
| Water | 4 |
| 2-Phenoxyethanol | 55 |
| 3-Heptyloxypropane-1,2-diol | 20 |

Example 11

|  | [% by weight] |
| --- | --- |
| Dehydroacetic acid | 10 |
| Benzoic acid | 10 |
| PHMBG | 1 |
| Water | 4 |
| 2-Phenoxyethanol | 55 |
| 3-Octyloxypropane-1,2-diol | 15 |
| Phenoxybutanol | 5 |

Example 12

|  | [% by weight] |
| --- | --- |
| Dehydroacetic acid | 7 |
| Benzoic acid | 13 |
| PHMBG | 2 |
| Water | 8 |
| 2-Phenoxyethanol | 60 |
| 3-Dodecyloxypropane-1,2-diol | 10 |

Example 13

|  | [% by weight] |
|---|---|
| Dehydroacetic acid | 10 |
| Benzoic acid | 10 |
| PHMBG | 1 |
| 2-Phenoxyethanol | 64 |
| 3-(2-Ethylhexyloxy)propane-1,2-diol | 15 |

Example 14

|  | [% by weight] |
|---|---|
| Dehydroacetic acid | 5 |
| Benzoic acid | 15 |
| PHMBG | 1 |
| Water | 4 |
| Phenoxypropanol | 65 |
| 3-(2-Ethylhexyloxy)propane-1,2-diol | 10 |

The invention has been described in detail with particular reference to certain preferred embodiments thereof, but it will be understood that variations and modifications can be effected within the spirit and scope of the invention.

We claim:

1. A preservative for compositions having an aqueous phase, said preservative consisting essentially of:
   a) from 10 to 30% by weight of an organic acid selected from the group consisting of benzoic acid, dehydroacetic acid, undecylenic acid, esters of such acids, salts of such acids, and mixtures thereof;
   b) from 40 to 80% by weight of an alcohol selected from the group consisting of benzyl alcohol, 2-phenoxyethanol, a phenoxybutanol and a phenoxypropanol; and
   c) from 0.5 to 10% by weight of a poly(hexamethylenebiguanide) salt in which the anion is selected from the group consisting of hydrochloride, acetate, lactate, benzoate, propionate, 4-hydroxybenzoate, sorbate and salicylate.

2. A preservative according to claim 1 which consists essentially of:
   a) benzoic acid or dehydroacetic acid;
   b) 2-phenoxyethanol; and
   c) poly(hexamethylenebiguanide) hydrochloride.

3. A preservative for compositions having an aqueous phase, said preservative consisting essentially of:
   a) from 10 to 30% by weight of an organic acid selected from the group consisting of benzoic acid, dehydroacetic acid, undecylenic acid, esters of such acids, salts of such acids, and mixtures thereof;
   b) from 40 to 80% by weight of an alcohol selected from the group consisting of benzyl alcohol, 2-phenoxyethanol, a phenoxybutanol and a phenoxypropanol;
   c) from 0.5 to 10% by weight of a poly(hexamethylenebiguanide) salt in which the anion is selected from the group consisting of hydrochloride, acetate, lactate, benzoate, propionate, 4-hydroxybenzoate, sorbate and salicylate; and
   d) from 0.1 to 20% by weight of a compound selected from the group consisting of 3-(2-ethylhexyloxy)-propane-1,2-diol, 3-heptyloxypropane-1,2-diol, 3-octyloxypropane-1,2-diol and 3-dodecyloxypropane-1,2-diol.

4. A preservative according to claim 3 which consists essentially of:
   a) benzoic acid or dehydroacetic acid;
   b) phenoxyethanol;
   c) poly(hexamethylenebiguanide) hydrochloride; and
   d) 3-heptyloxypropane-1,2-diol.

5. A preservative composition which comprises a preservative according to claims 1 or 3 and, in an amount up to 10% by weight of said preservative composition, a complexant selected from the group consisting of ethylenediaminetetraacetic acid or its salts, nitrilotriacetic acid, an aminoglycine, serinediacetic acid, isoserinediacetic acid, and mixtures thereof.

6. A preservative composition which comprises a preservative according to claims 1 or 3 and from 1 to 20% by weight of an additional biocide selected from the group consisting of chloroallyladamantane, hydroxybenzoic esters, 1,2-dibromo-2,4-dicyanobutane, 2-bromo-2-nitropropane-1,3-diol, 5-bromo-5-nitro-1,3-dioxane, imidazolidinylurea, a hydantoin and mixtures thereof.

7. A method for preserving compositions having an aqueous phase, which method comprises treating said compositions with from 0.01 to 2% by weight, based on the weight of active substance in the aqueous composition, of a preservative consisting essentially of:
   a. from 10 to 30% by weight of an organic acid selected from the group consisting of benzoic acid, dehydroacetic acid, undecylenic acid, esters of such acids, salts of such acids, and mixtures thereof;
   b. from 40 to 80% by weight of an alcohol selected from the group consisting of benzyl alcohol, 2-phenoxyethanol, a phenoxybutanol and a phenoxypropanol; and
   c. from 0.5 to 10% by weight of a poly(hexamethylenebiguanide) salt in which the action is selected from the group consisting of hydrochloride, acetate, lactate, benzoate, propionate, 4-hydroxybenzoate, sorbate and salicylate.

8. A method for preserving compositions having an aqueous phase, which method comprises treating said compositions with from 0.01 to 2% by weight, based on the weight of the active substance in the aqueous compositions, of a composition consisting essentially of:
   a) from 10 to 30% by weight of an organic acid selected from the group consisting of benzoic acid, dehydroacetic acid, undecylenic acid, esters of such acids, salts of such acids, and mixtures thereof;
   b) from 40 to 80% by weight of an alcohol selected from the group consisting of benzyl alcohol, 2 phenoxyethanol, a phenoxybutanol and a phenoxypropanol;
   c) from 0.5 to 10% weight of a poly(hemamethylenebiguanide) salt in which the anion is selected from the group consisting of hydrochloride, acetate, lactate, benzoate, propionate, 4-hydroxybenzoate, sorbate and salicylate; and
   d) from 0.1 to 20% by weight of a compound selected from the group consisting of 3-(2-ethylhexyloxy)-propane 1,2 diol, 3 heptyloxypropane-1,2-diol 3-octyloxypropane-1,2-diol and 3-dodecyloxypropane-1,2-diol.

* * * * *

UNITED STATES PATENT AND TRADEMARK OFFICE
CERTIFICATE OF CORRECTION

PATENT NO. : 5,670,160
DATED : September 23, 1997
INVENTOR(S) : Heinz Eggensperger, Karl-Heinz Diehl, Peter Oltmanns It is certified that error appears in the above-identified patent and that said Letters Patent is hereby corrected as shown below:

In column 16, line 45, delete "compositions" and insert --composition--.

In column 16, line 56, delete "(hemamethylenebiguanide)" and insert --(hexamethylenebiguanide)--.

Signed and Sealed this

Second Day of December, 1997

Attest:

BRUCE LEHMAN

Attesting Officer

Commissioner of Patents and Trademarks